United States Patent
Gilligan et al.

(10) Patent No.: US 7,858,048 B2
(45) Date of Patent: Dec. 28, 2010

(54) MICROFLUIDIC SYSTEM

(75) Inventors: Mark Peter Timothy Gilligan, Royston (GB); Philip James Homewood, London (GB); John Philip Briant, Letchworth Garden City (GB); Andrew Mark Lovatt, Harlton (GB)

(73) Assignee: Syrris Limited (GB)

( * ) Notice: Subject to any disclaimer, the term of this patent is extended or adjusted under 35 U.S.C. 154(b) by 771 days.

(21) Appl. No.: 10/924,599

(22) Filed: Aug. 24, 2004

(65) Prior Publication Data

US 2005/0052509 A1 Mar. 10, 2005

(30) Foreign Application Priority Data

Aug. 29, 2003 (GB) ................... 0320337.9

(51) Int. Cl.
*B81B 7/00* (2006.01)
(52) U.S. Cl. .................. 422/130; 422/129; 977/904
(58) Field of Classification Search ........... 417/441, 417/521, 531, 532; 222/61, 389, 394, 399; 422/100, 129–242; 977/904
See application file for complete search history.

(56) References Cited

U.S. PATENT DOCUMENTS

| | | | | |
|---|---|---|---|---|
| 5,580,523 A * | 12/1996 | Bard | ................. | 422/50 |
| 5,738,728 A * | 4/1998 | Tisone | ................. | 118/638 |
| 5,738,783 A * | 4/1998 | Shirota et al. | ........... | 210/198.2 |
| 5,743,960 A * | 4/1998 | Tisone | ................. | 118/683 |
| 6,027,479 A * | 2/2000 | Alei et al. | ................. | 604/131 |
| 6,137,501 A * | 10/2000 | Wen et al. | ............. | 346/140.1 |
| 6,368,562 B1 | 4/2002 | Yao | .................. | 422/100 |
| 6,409,832 B2 * | 6/2002 | Weigl et al. | ............. | 117/206 |
| 6,416,642 B1 * | 7/2002 | Alajoki et al. | ........... | 204/451 |
| RE38,281 E * | 10/2003 | Tisone | ................. | 422/100 |
| 6,632,655 B1 * | 10/2003 | Mehta et al. | ............. | 506/14 |
| 6,699,384 B1 * | 3/2004 | Lin et al. | ............... | 205/792 |
| 6,866,762 B2 * | 3/2005 | Gascoyne et al. | ........ | 204/547 |
| 6,892,525 B2 * | 5/2005 | Guiheen et al. | ........... | 60/200.1 |
| 6,902,934 B1 * | 6/2005 | Bergh et al. | ............... | 436/37 |
| 2001/0041357 A1 * | 11/2001 | Fouillet et al. | ........... | 435/91.1 |
| 2002/0064482 A1 | 5/2002 | Tisone et al. | ............. | 422/100 |
| 2003/0156995 A1 * | 8/2003 | Gilligan et al. | ........... | 422/100 |
| 2004/0109792 A1 * | 6/2004 | Karlsson et al. | .......... | 422/99 |
| 2005/0214184 A1 * | 9/2005 | Chambers et al. | .......... | 422/193 |

FOREIGN PATENT DOCUMENTS

| | | |
|---|---|---|
| EP | 1221617 A2 | 12/2001 |
| WO | WO 03/008102 A1 | 7/2002 |
| WO | WO 02070118 | 9/2002 |

* cited by examiner

*Primary Examiner*—Devon C Kramer
*Assistant Examiner*—Patrick Hamo
(74) *Attorney, Agent, or Firm*—Ballard Spahr LLP

(57) ABSTRACT

A microfluidic system comprising a microchannel (2), a pressurized reservoir (3-5) of fluid and a positive displacement pump (7-9) downstream of the reservoir for pumping the fluid from the reservoir to the microchannel.

11 Claims, 6 Drawing Sheets

MICROFLUIDIC SYSTEM

CROSS REFERENCE TO RELATED APPLICATIONS

The present application claims priority to Great Britain Application No. 0320337.9, filed Aug. 29, 2003, which application is incorporated herein fully by this reference.

BACKGROUND OF THE INVENTION

Field of the Invention

The present invention relates to a microfluidic system.

One of the current challenges in microfluidics is pumping at a very low flow rate, in particular in the 10 nl/min-10 µl/min range (or even as much as 1000 µl/min). A common method is Electro Osmotic Flow (EOF), also known as electrokinetic flow, used in microreactors and µTAS devices such as biological analysis chips. EOF works well if the properties of the fluid, such as Zeta potential and viscosity, are known. The main applications of such a technique are water based biological microfluidic systems where reagents are supplied with the system and have fixed and known properties. For other situations where the fluid properties are unknown EOF is less applicable, as fluid flow rate and flow direction are unpredictable.

Other methods employed for generating low flow rates include pumping with gas pressure and a range of microfabricated diaphragm pumps that have been made in silicon/glass and laminated polymer chips. There are several drawbacks with these methods including flow rate varying with fluid viscosity and back pressure and also pulsing of flow (from the diaphragm pumps).

Positive displacement pumping using a syringe pump (with electromechanical drive) and valves is a popular approach for delivering a continuous & non-pulsing flow of fluid to microfluidic systems. With displacement pumping flow rate can be controlled very accurately and does not vary with the fluid properties or pumping pressure over a wide range of operation.

SUMMARY OF THE INVENTION

We have experimented with glass/PTFE syringes having a volume ranging from 0.5 µl-500 µl with a travel of around 10-100 mm and an inside diameter ranging from 0.1-5 mm. In a syringe of this size, surface tension effects dominate over gravitational effects. The result is that gas bubbles in the syringe tend to get stuck in the bore rather than rising to the top.

When all of the fluid is expelled from the syringe bore, the bubble typically gets trapped in the connections from the syringe to the valves and gets pulled back into the syringe on the second and consecutive strokes. Bubbles can also get trapped in the valves. During each stroke cycle the bubble gets compressed and expanded with a resulting decrease in total pump flow rate. The effect of this is that fluid flow rate is unknown and unpredictable transients can occur in the flow. Cases have been observed where the net flow rate drops to zero.

In order to solve this problem the bore diameter of the syringe can be increased so that the bubbles are ejected. This would solve the problem, but results in an increase in the dead volume of the pump which is undesirable, and also increases the minimum flow rate possible. Alternatively, it is possible to accept that bubbles will be there and run the system under constant pressure conditions so that bubble expansion and compression does not occur. We have used this approach and it works well, but it is complicated and prohibitively expensive to use commercially.

The present invention therefore aims to provide a microfluidic system which reduces bubble formation.

According to the present invention there is provided a microfluidic system comprising a microchannel, a pressurised reservoir of fluid and a positive displacement pump downstream of the reservoir for pumping the fluid from the reservoir to the microchannel.

By pressurizing the reservoir, the formation of bubbles of dissolved gas can be reduced or eliminated. The majority of fluid reagents will have gasses dissolved at room temperature and pressure. By increasing the pressure, dissolved gasses will have a tendency to stay in solution rather than come out.

Further, increasing the system pressure increases the boiling points of the fluids in the system. This allows the system to operate at a higher temperature without the risk of boiling, resulting in faster reaction rates. For example a reaction carried out in Ethyl Acetate (reaction solvent) is normally limited to running at 77 degrees Centigrade (boiling point of solvent at atmospheric pressure). By increasing the pressure by just a couple of Bar, it is possible to run the reaction at 110 degrees Centigrade. This typically results in an eightfold increase in reaction rate (Arrhenius rate law).

Also, if a solvent is present, solvent evaporation will significantly reduce at the higher pressure. This is because the solvent boiling point increases with pressure. This has the added advantage that the pump will work over a larger temperature range.

Preferably, a number of fluids are supplied to the microchannel, each fluid being supplied under pressure from the reservoir. Each fluid is pressurably supplied from a respective reservoir, although more than one fluid stream may be supplied from a common reservoir.

Preferably, the microchannel has an outlet which is pressurised to the same degree as the, or each, reservoir so that the whole system operates at equal pressure. This ensures that, in a system that employs passive valves (also known as check valves) in the pumps, there will be no flow through the system as a result of pressure differentials between the inlet and outlet. The system is also generally simpler to implement than a differentially pressurised system.

Alternatively, the outlet may be pressurised to a different extent than the, or each, reservoir. If it is at a higher pressure, then passive valves could also be used without the risk of forward flow through the system. This has the additional benefit that variations in pressure in the input reservoirs would not result in flow variations through the system. However, preferably the outlet is pressurised to a lesser extent than the, or each, reservoir and may even be left open to atmosphere. This has the advantage that the pump can have a lower pressure rating as it only has to push against the frictional pressure drop across the microchannel. This arrangement will require the use of active valves to stop the pressure difference causing additional flow through the system as a result of the pressure differential. A throttle may be provided on the outlet side of the microchannel to ensure that the pressure within the microchannel does not drop to the extent that the fluids will start to degas and boil.

An alternative, preferred approach would be to use a variable throttle that is controlled such that the pressure of the fluid as it exits the microfluidic system (before the throttle) is kept constant and equal to or above the input reservoir pressure. This device would work in a similar way to a gas pressure regulator.

The system will generally have one or more valves to control the flow of fluid along the system feed lines. These feed lines and valves will have a pressure drop associated with them. Preferably, the pressure applied to the reservoirs is greater than the pressure drop across the feed lines and valves as this will avoid cavitation of the fluid.

In order to pressurise the, or each, reservoir, the reservoir is preferably provided with a gas supply at a pressure greater than atmospheric. However, alternatively, the, or each, reservoir may be pressurised by a plunger to which a force is applied, for example by a spring or a mass.

Although reference has been made to an outlet, it should be understood that there could be more than one outlet, for example, an outlet line from the device could be diverted to two or more reservoirs via a flow diverter.

The pressure applied is preferably 1.1-10 bar (absolute pressure).

In an alternative system, the liquid in the reservoir is a solvent, and the reagents may be supplied from separate reservoirs. In this case, the system is preferably arranged such that the pressurised reservoir of fluid contains a solvent, a sample valve is provided downstream of the pump and upstream of the microchannel, a reagent stream leads to the sample valve, and a sample loop leads to and from the sample valve, the sample valve being arranged to form a stream comprising slugs of reagent entrained in a stream of solvent in the sample loop and to supply the stream to the microchannel driven by the pump.

Such an arrangement avoids the need for a pressurised reagent to be passed through a pump, and this can have advantages in certain situations. Positive displacement pumps have dead volume and also use sliding seals. When a new reaction is run new reagents are typically used and the old ones need to be purged out of the pumps. This can be quite time consuming (as a result of the dead volume) and wastes solvent and reagents (the volume of solvent required for a purge might be 10-20 times the dead volume of the pump). Reagents are more chemically aggressive when compared with solvents and can damage sliding seals and other parts of the pump. By injecting reagents via a sample loop/sample valve, the pump only comes into contact with solvent. Different reagents can be injected into the sample loop without needing to purge the pumps. This allows much faster experimental operation and also prolongs the life of the pumps. Further to this robotic injection of reagents into sample loops is a relatively simple thing to do and is well know, whereas automating the process to change reagents in reservoirs and pumps is lengthy/difficult.

Preferably, the, or each, reservoir is provided by an outer housing, the lower end of which is engaged with a support thereby forming a seal, an inner housing within the outer housing engaged with the support to form a second seal, the inner housing being arranged to receive a fluid and having a fluid outlet through the support, a supply of pressurised gas into a space between the inner and outer housing, and a sealable interface on the outer housing allowing injection of fluids into the reservoir.

BRIEF DESCRIPTION OF THE DRAWINGS

Examples of microfluidic systems in accordance with the present invention will now be described with reference to the accompanying drawings, in which.

DESCRIPTION OF THE PREFERRED EMBODIMENTS

The examples shown are microreactors. Although, the invention is equally applicable to other microfluidic systems such as Micro Total Analysis Systems (μTAS), or lab on a chip devices.

The terms "microfluidic system", "microreactor" and "microchannel" are believed to be terms which are clearly understood in the art. The terms are best understood functionally as relating to systems/reactors/channels which are sufficiently small that diffusional mixing predominates and efficient heat transfer occurs, resulting in optimal reaction conditions in the microchannel. The dimensions should be sufficiently small that the flow results in a low Reynold's number ($<10^3$) and a predominantly laminar flow regime.

Generally at its narrowest point, the reactor/channel should have, in cross-section, a maximum internal dimension of 5-500 μm, and preferably 5-250 μm. However, it is possible to envisage a channel which has a long thin cross-section having a dimension greater than 500 μm, but which still operates as a microchannel as it is small in other dimensions. Therefore, it might be more appropriate to define a microfluidic system/microreactor/microchannel as having, at its narrowest part, a cross-section in a plane perpendicular to the direction of flow which is sized so that the largest circle which can be drawn in a cross-section has a diameter of <500 μm (and preferably <250 μm). In other words, if the cross-section is such that a circle of >500 μm can be drawn within the cross-section, it will not operate as a microchannel.

Figure 1:
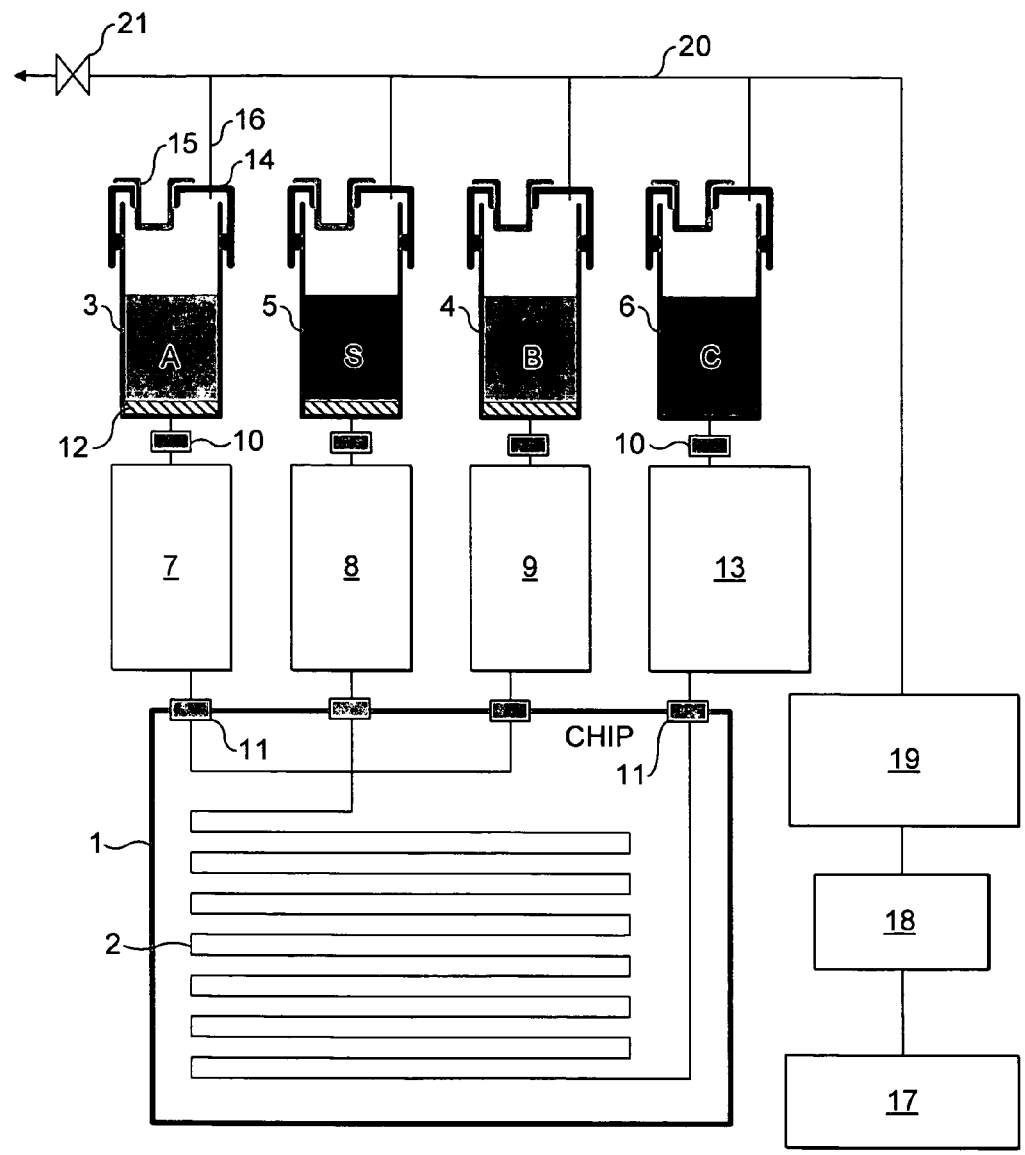
FIG. 1 is a schematic representation of a first system.
Figure 3:
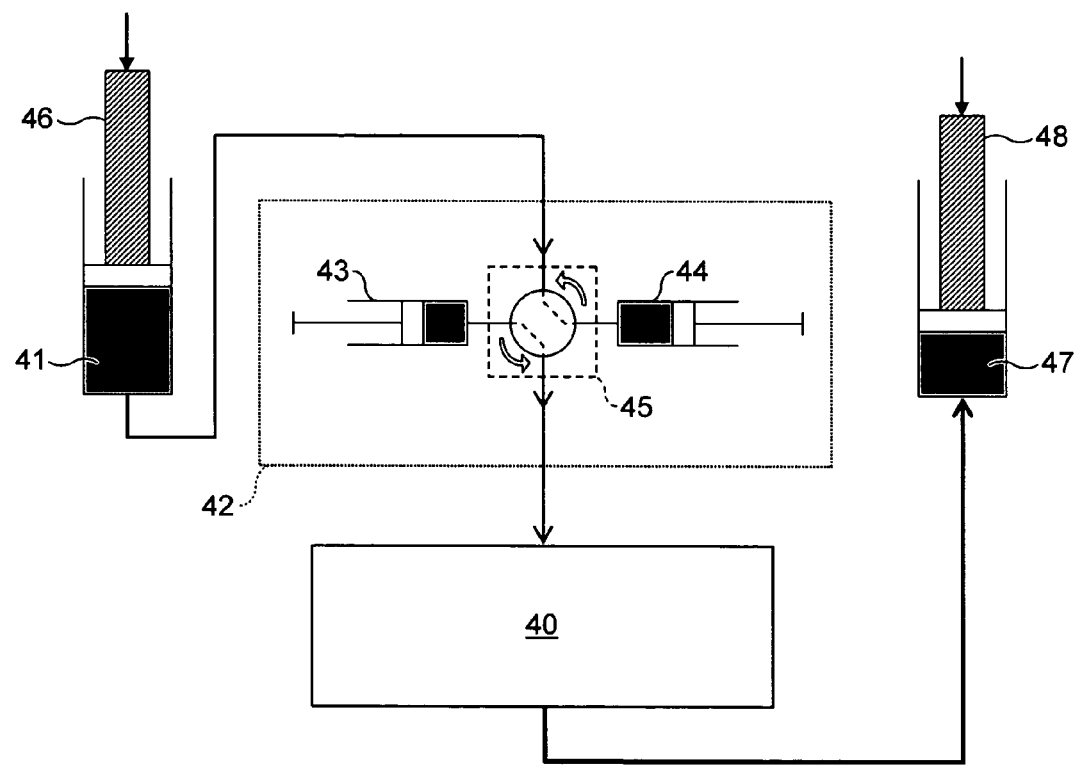
FIG. 3 is a schematic representation of an alternative means of pressurizing the reservoirs.

The example shown in FIG. 1 is a microreactor in which a reaction takes place on a chip 1 in reaction channel 2. The reactor is fed with a first reagent A from first reservoir 3 and a secondary reagent B from second reservoir 4. A third reservoir 5 supplies solvent S to the channel. The reactant C from the reaction channel 2 is fed to a fourth reservoir 6. Each of the first 3, second 4 and third 5 reservoirs is connected to the chip 1 via a first 7, second 8 and third 9 pump. The pumps are syringe pumps which are well known in the art (as shown in FIG. 3 described below). Screw fittings or similar connections 10 are provided between each pump and each reservoir and a gasket seal 11 is provided to seal each pump to the chip. A fluid filter 12 is provided across the outlet of each reservoir.

A control system (not shown) is provided to control the operation of the pumps to supply the reagents A, B and solvent S according to the requirements of the reaction. A sensor 13 monitors the progress of the reaction and provides feedback to the control system.

In the example shown in FIG. 1, each of the first to fourth reservoirs 3-6 are pressurised. Each reservoir 3-6 is essentially a test tube which is sealed with a cap 14. The cap 14 has a pierceable septum 15 allowing the reservoir to be topped-up. Also in the cap is a gas inlet 16. A common gas supply is provided to all of the reservoirs. This takes the form of a source of gas 17 which is a cylinder of lab gas, such as nitrogen. This gas is supplied through a pressure regulator 18 and a pressure sensor 19 which ensures that the gas pressure is maintained within the desired limits. The gas is supplied to a manifold 20 which then directs the gas to the inlets 16 of all of the reservoirs. A gas bleed valve 21 is provided to ensure that a constant low flow of gas is provided to allow the regulator to function.

The effect of this arrangement is that the entire system is pressurised at a constant level.

Figure 2:
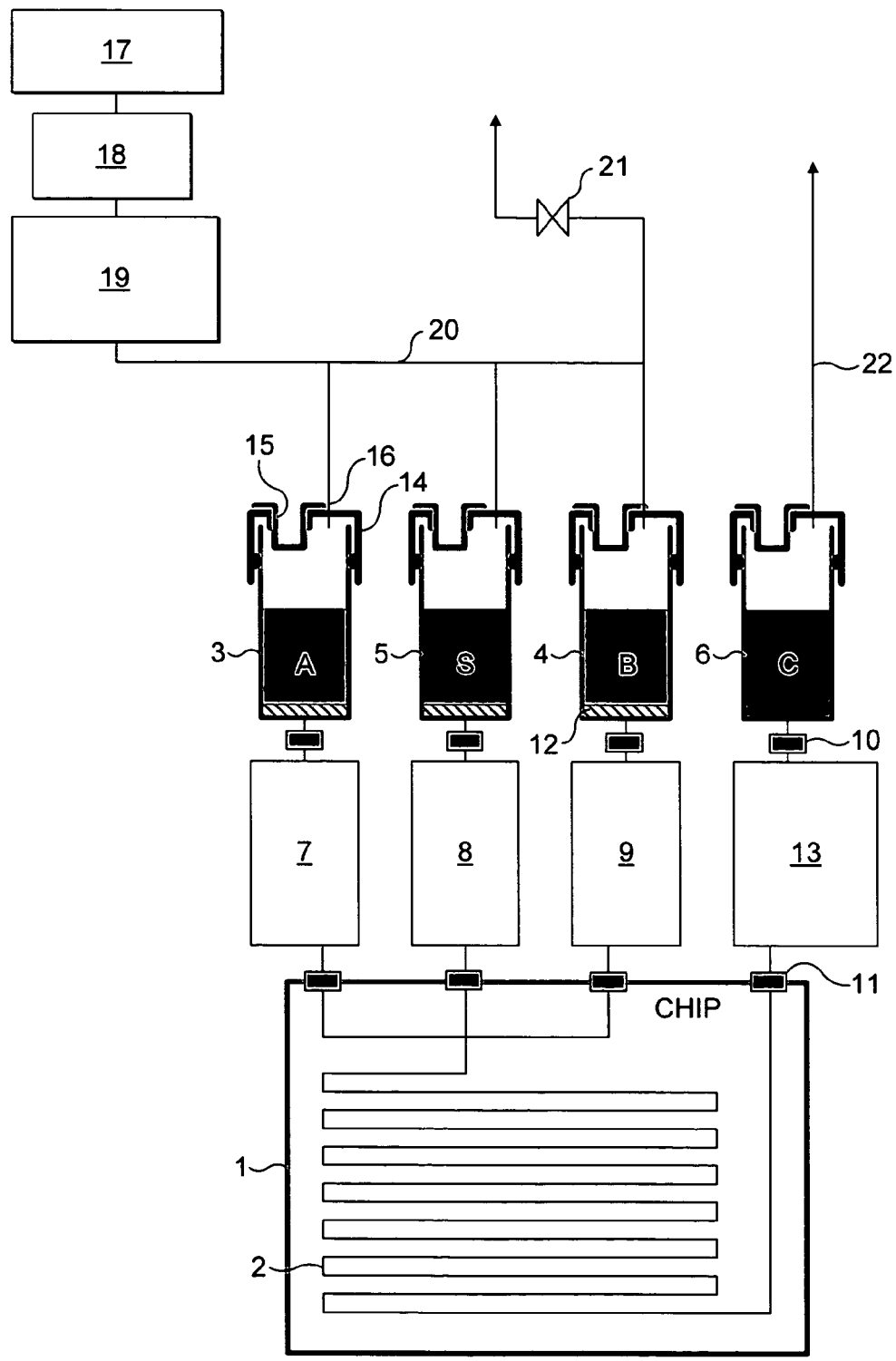
FIG. 2 is a schematic representation of a second system.

An alternative arrangement is shown in FIG. 2 where the same components are designated with the same reference numerals. The only difference in the FIG. 2 arrangement is that the fourth reservoir 6 is not connected to the gas manifold 20 but is either left open to the atmosphere or is connected to an independently controllable pressure source along line 22.

A sampling valve may be provided between the chip 1 and the fourth reservoir 6 allowing a proportion of the reagent to be diverted to an external system such as a High Performance Liquid Chromatography (HPLC) analysis system in which the reagent is analysed.

FIG. 3 shows an example of a microfluidic system with an alternative way of pressurizing the reservoirs. In this case, the microfluidic system (e.g. a microreactor chip) 40 is supplied with fluid from a single reservoir 41 via a positive displacement pump 42 this positive displacement pump takes the form of a pair of syringes 43, 44 and an active valve 45 which are controlled by a system controller. The active valve is configured to allow a first syringe 43 to be connected to the microfluidic system 40 to supply it with fluid while the second syringe 44 is connected to the reservoir 41 to be refilled. When the plungers in the syringes reach the end of their travel, the valve 45 is moved to a second position in which the positions are reversed allowing the second syringe 44 to supply the microfluidic system 40 while the first syringe 43 is refilled from the reservoir. This provides a constant flow to the microfluidic system 40. This arrangement can also be applied to the pumps 7-9 shown in FIGS. 1-3.

Rather than pressurizing the reservoir 41 with gas pressure, the reservoir 41 is provided with a plunger 46 to which a force is applied either by a mass or a spring in order to pressurise the reservoir 41. The outlet reservoir 47 is similarly provided with a plunger 48 to which the same or a lesser force can be applied. Alternatively, this can be left open to the atmosphere.

Figure 4:
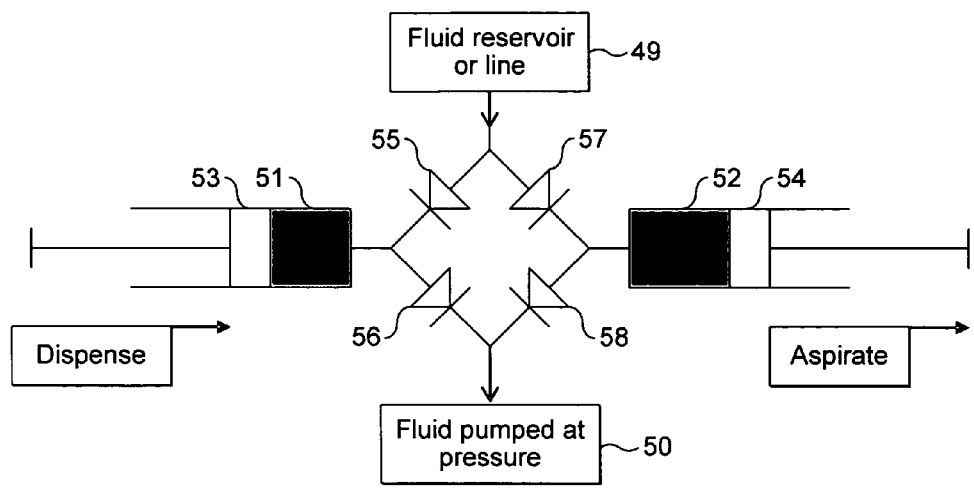
FIG. 4 is a schematic representation of an alternative pump configuration.
Figure 5:
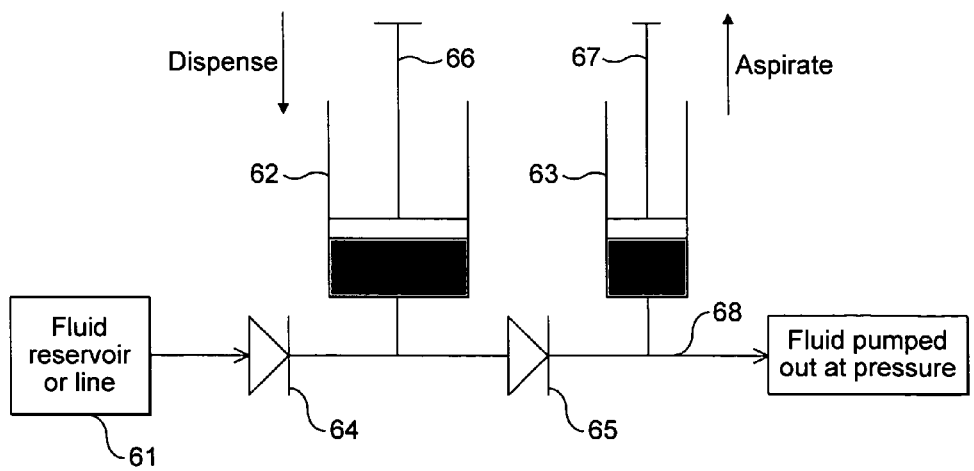
FIG. 5 is a schematic representation of a second alternative pump configuration.

As an alternative to the pump arrangement of FIG. 3, two alternative arrangements are shown in FIGS. 4 and 5 respectively. These may be used with any of the arrangements of FIG. 1 to 3.

In FIG. 4 fluid is fed from a reservoir 49 to a microfluidic system 50 using a first 51 and second 52 syringe. The first syringe has a first plunger 53 and the second syringe has a second plunger 54. Four passive one-way valves 55-58 are connected as follows. First valve 55 allows flow from the reservoir 49 to first syringe 51. Second valve 56 allows flow from the first syringe 51 to microfluidic device 50. Third valve 57 allows flow from the reservoir 49 to second syringe 52 and third valve 58 allows flow from the second syringe 52 to the microfluidic device 50. The plungers 53, 54 operate in anti-phase, such that when the first plunger 53 is on a downstroke, the second plunger 54 is on an upstroke. At this time, fluid is dispensed from the first syringe 51 via second valve 56, while fluid is drawn from the reservoir 49 into the second syringe 52 via third valve 57. When the plungers move in the opposite direction, fluid is dispensed from the second syringe 52 via fourth valve 58, while syringe 51 is replenished from the fluid reservoir 49 via first valve 55.

A further alternative pump is shown in FIG. 5. This also uses a pair of syringes and passive one-way valves. Fluid is drawn from a reservoir 61 by first 62 and second 63 syringes connected in series. A first one-way valve 64 is provided between the fluid reservoir and the first syringe 62 and a second one-way valve 65 is provided between the two syringes. The first syringe 62 has twice the volume of the second syringe 63. The syringes are driven in anti-phase such that when a plunger 66 in the first syringe is being withdrawn, a plunger 67 in the second syringe 63 is being pushed into the syringe and vice versa. Thus, as the plunger 66 is withdrawn from the first syringe 62, fluid is sucked into the syringe from the reservoir 61 via first one-way valve 64. At the same time, plunger 67 is being pushed into the second syringe 63 to dispense fluid out of line 68. When the plungers travel in opposite directions, the first syringe 62 dispenses twice the volume of liquid as the second syringe 63 through one-way valve 65. Half of this is sucked into second syringe 63 for dispensing on the following stroke, while the other half is supplied to line 68.

Figure 6:
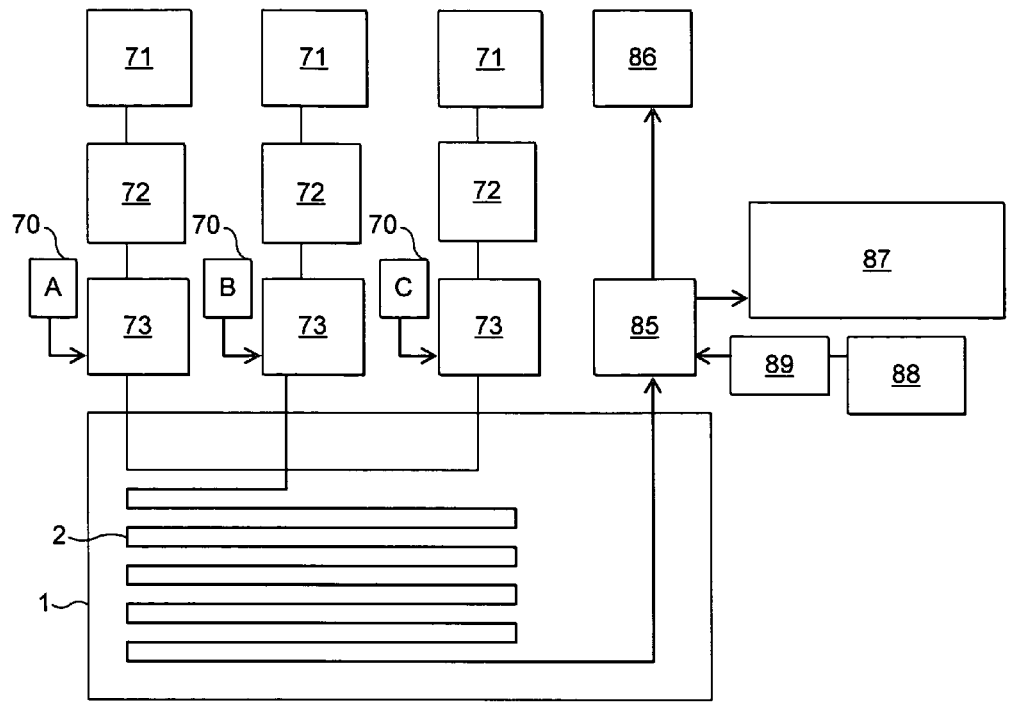
FIG. 6 is a schematic representation of a third system.

A third system is illustrated in FIG. 6. As with the previous two systems, this system comprises a chip 1 with a reaction channel 2 to which three reagents A, B and C are supplied. However, in this system, the mechanism for supplying the reagents is different. The reagents are contained in reservoirs 70 which may be pressurised, but preferably are not. Instead, the pressurised reservoirs are provided by solvent reservoirs 71. In FIG. 6 one pressurised solvent reservoir 71 is provided for each reagent. However, there could be a common pressurised reservoir of solvent for all of the reagents.

Each reagent has an associated pump 72 which pumps the solvent from the pressurised reservoir 71 to a sample valve 73.

Figure 7A:
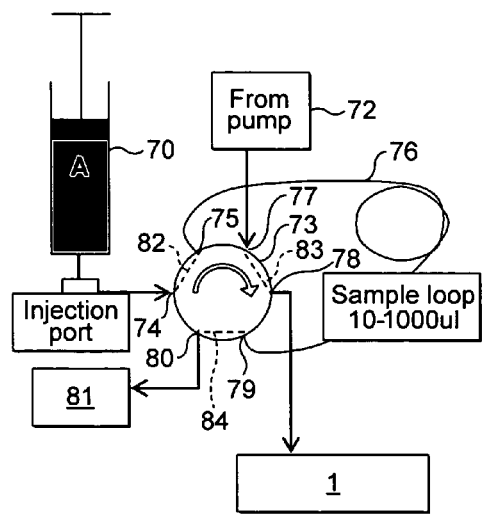
FIGS. 7A and 7B are schematic diagrams showing in more detail the operation of the sample valves of FIG. 6.
Figure 7B:
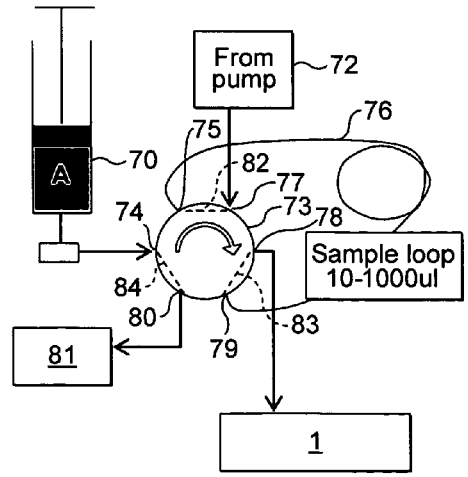

The operation of the sample valves is described in greater detail with reference to FIGS. 7A and 7B. FIG. 7A shows the sample valve 73 in a position to charge the sample loop with a reagent, while FIG. 7B shows the sample valve in a position to discharge fluid from the sample loop to the chip 1.

The sample valve 73 is provided with six ports as follows:
An inlet port 74 for reagent from the reservoir 70
An outlet port 75 to sample loop 76
An inlet 77 port for solvent from the pump 72
An outlet port 78 for fluid to the chip 1
An inlet port 79 for fluid from the sample loop 76
An outlet port 80 to waste 81

The sample valve 73 comprises three internal passages 82, 83, 84. The sample loop 76 is shown outside the sample valve 73 and this will normally be the case. However, it is possible to provide the sample loop within a rotor of the sample valve. In the first configuration shown in FIG. 7, the first passage 82 connects ports 74 and 75, the second passage 83 connects ports 77 and 78 and the third passage 84 connects ports 79 and 80. In the second configuration shown in FIG. 7B, the sample valve 73 has been rotated through 60 degrees. In this configuration, the first passage 82 connects ports 75 and 77, the second passage 83 connects ports 78 and 79, and the third passage 84 connects ports 80 and 74. It should be noted that the three lines are identical, such that the sample valve effectively has two operative positions as shown in FIGS. 7A and 7B.

With the sample valve 73 in the position shown in FIG. 7A, reagent is injected from reservoir 70 into the sample loop 76 along the first line 82. Residual fluid in the sample loop 76 is as displaced along third line 84 to waste 81. At the same time, solvent is pumped from pump 72 to chip 1. In this configuration, a slug of reagent is formed in the sample loop. The sample valve 73 is then moved to the second position as shown in FIG. 7B. In this position the pump 72 pumps further solvent into the sample loop 76 thereby displacing the slug of reagent along the second line 83 into the chip 1.

As shown in FIG. 6, the reaction channel 2 leads to a further sample valve 85 from which the fluid is either diverted to pressurised waste reservoir 86, or to the high performance liquid chromatography system 87 for analysis. A further solvent reservoir 88 and associated pump 89 are provided to displace fluid from the sample valve 85.

Figure 8:
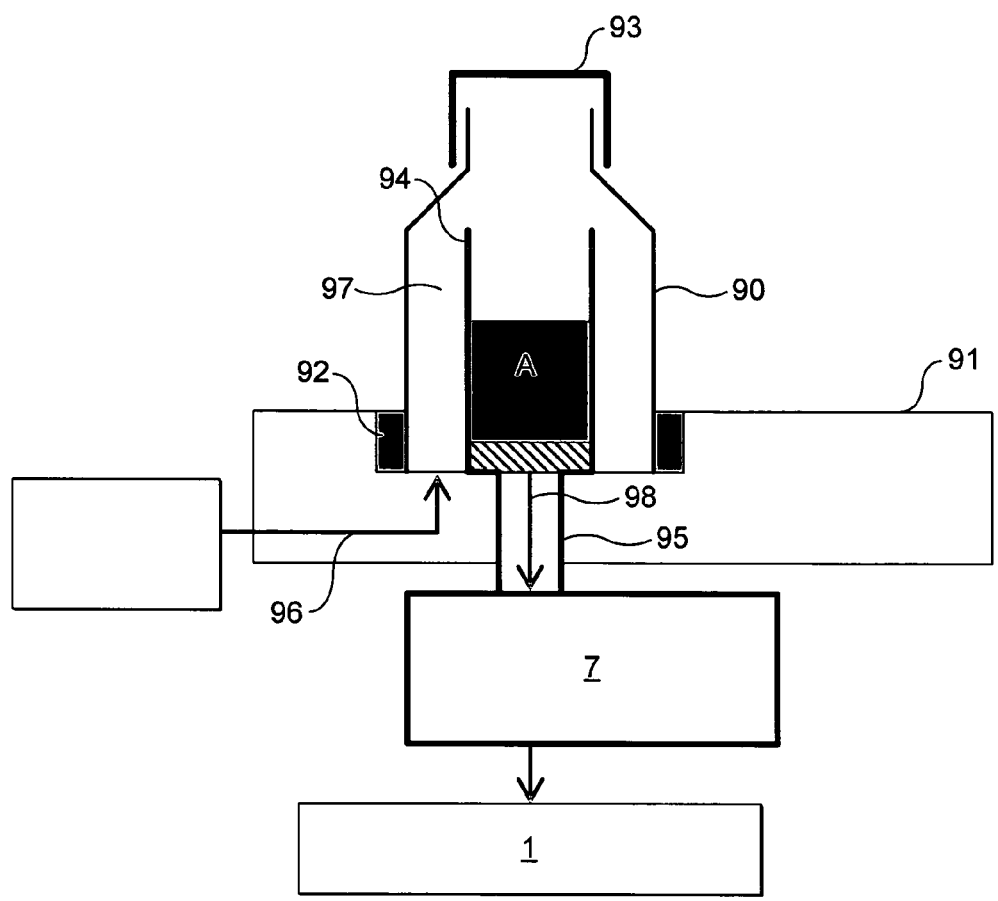
FIG. 8 is a schematic diagram showing a reservoir construction in greater detail.

FIG. 8 shows the current preferred construction for a reservoir. This may either be a reactant reservoir 3, 4, 5 as shown in FIGS. 1 and 2 or a solvent reservoir 6, 71 as shown in FIGS. 1, 2 and 6.

The reservoir comprises a housing in the form of an outer glass tube 90. This is screwed into an underlying framework 91 via screw threads 92. The glass tube 90 is sealed, at its top end, by a rubber septum 93 which allows the addition of a further reagent with a syringe. Within the glass tube 90 is an inner glass reservoir 94, containing the reagent A. This also screws into the framework 91 at screw threads 95. The two screw thread attachments could alternatively be a clip, latch or rotate and lock attachment. A feed for pressurised inert gas 96 is provided through the framework 91 and into an annular space 97 between the outer glass tube and the inner glass reservoir. The inner reservoir 94 has an outlet 98 leading to pump 7 and then to chip 1.

With this design, the reservoir can be readily assembled and dismantled simply by unscrewing the outer glass tube 90 and inner glass reservoir 98, both of which readily provide sealed interfaces in situ. Further, the septum 93 provides for the simple addition of new reagents to the reservoir even when the reservoir is pressurised.

What is claimed is:

1. A microreactor comprising a reaction microchannel, a plurality of pressurized reservoirs of different liquids pressurized to increase the pressure of the liquids to decrease bubble formation and a plurality of positive displacement pumps downstream of the reservoirs for pumping the liquids from the reservoirs to the microchannel.

2. A microreactor according to claim 1, wherein the microchannel has an outlet which is pressurized to the same degree as at least one of the reservoirs.

3. A microreactor according to claim 1, wherein the microchannel has an outlet which is pressurized to a greater extent than at least one of the reservoirs.

4. A microreactor according to claim 1, wherein the microchannel has an outlet and a throttle is associated with the outlet, the throttle arranged to control the pressure upstream of the throttle to be at a level equal to or greater than the pressure in at least one of the reservoirs.

5. A microreactor according to claim 1, wherein the microchannel has an outlet which is pressurized to a lesser extent than at least one of the reservoirs.

6. A microreactor according to claim 1, wherein the microchannel has an outlet which is open to atmosphere.

7. A microreactor according to claim 1, further comprising one or more valves to control the flow of liquids along the system feed lines, wherein the pressure applied to the reservoirs is greater than the pressure drop across the feed lines and valves.

8. A microreactor according to claim 1, wherein the reservoirs are provided with a gas supply at a pressure greater than atmospheric.

9. A microreactor according to claim 1, wherein the reservoirs are pressurized by a plunger to which a force is applied.

10. A microreactor according to claim 1, wherein at least one of the pressurized reservoirs of liquid contains a solvent, a sample valve is provided downstream of the pumps and upstream of the microchannel, a reagent stream leads to the sample valve, and a sample loop leads to and from the sample valve, the sample valve being arranged to form a stream comprising slugs of reagent entrained in a stream of solvent in the sample loop and to supply the stream comprising slugs or reagent entrained in a stream of solvent to the microchannel driven by a pump.

11. A microreactor according to claim 1, wherein the at least one reservoir is provided by an outer housing, the lower end of which is engaged with a support thereby forming a seal, an inner housing within the outer housing engaged with the support to form a second seal, the inner housing being arranged to receive a liquid and having a liquid outlet through the support, a supply of pressurized gas into a space between the inner and outer housing, and a sealable interface on the outer housing allowing injection of liquid into at least one reservoir.

* * * * *